(12) United States Patent
Oda

(10) Patent No.: US 10,220,149 B2
(45) Date of Patent: Mar. 5, 2019

(54) SYRINGE

(71) Applicant: DAICEL CORPORATION, Osaka-shi, Osaka (JP)

(72) Inventor: Shingo Oda, Tatsuno (JP)

(73) Assignee: Daicel Corporation, Osaka (JP)

( * ) Notice: Subject to any disclaimer, the term of this patent is extended or adjusted under 35 U.S.C. 154(b) by 0 days.

(21) Appl. No.: 15/694,615

(22) Filed: Sep. 1, 2017

(65) Prior Publication Data

US 2018/0036485 A1 Feb. 8, 2018

Related U.S. Application Data

(63) Continuation of application No. 13/824,156, filed as application No. PCT/JP2011/071211 on Sep. 16, 2011, now Pat. No. 9,750,880.

(30) Foreign Application Priority Data

Sep. 17, 2010 (JP) ................................. 2010-210193

(51) Int. Cl.
*A61M 5/30* (2006.01)
*A61M 5/46* (2006.01)
*A61M 5/20* (2006.01)

(52) U.S. Cl.
CPC ................ *A61M 5/30* (2013.01); *A61M 5/46* (2013.01); *A61M 5/2046* (2013.01)

(58) Field of Classification Search
CPC .... A61M 5/30; A61M 5/2046; A61M 5/2053; A61M 5/46

(Continued)

(56) References Cited

U.S. PATENT DOCUMENTS 2,704,542 A   3/1955 Scherer
6,406,456 B1   6/2002 Slate et al.
(Continued)

FOREIGN PATENT DOCUMENTS

CN   1436088 A   8/2003
EP   2214756 A1   8/2010
(Continued)

OTHER PUBLICATIONS

Joy Baxter, Samir Mitragotri, "Jet-induced skin puncture and its impact on needle-free jet injections: Experimental studies and a predictive model", Journal of Controlled Release (U.S.A.) 106(2005), p361-373.

(Continued)

*Primary Examiner* — Phillip A Gray
(74) *Attorney, Agent, or Firm* — Knobbe Martens Olson & Bear LLP

(57) ABSTRACT

It is possible to feed an injection objective substance to a depth of a skin structure of an objective living body without using any injection needle. A syringe having no injection needle comprises an enclosing unit which encloses the injection objective substance, a pressurizing unit which pressurizes the injection objective substance enclosed in the enclosing unit, and a flow passage unit which defines a flow passage so that the injection objective substance, which is pressurized by the pressurizing unit, is allowed to inject to an injection target area. The pressurizing unit has a first pressurizing mode in which a pressure applied to the injection objective substance in the pressurizing unit is raised to a first peak pressure in order to form a penetrating passage in the injection target area, and then the pressure applied to the injection objective substance is lowered to a waiting pressure, and a second pressurizing mode in which the injection objective substance having the waiting pressure is (Continued)

pressurized so that the pressure applied to the injection objective substance is raised to a second peak pressure to inject a predetermined injection amount of the injection objective substance.

9 Claims, 7 Drawing Sheets

(58) Field of Classification Search
USPC .............................................. 604/68–70, 500
See application file for complete search history.

(56) References Cited

U.S. PATENT DOCUMENTS

| | | | |
|---|---|---|---|
| 6,837,866 | B1 | 1/2005 | Alexandre et al. |
| 7,150,409 | B2 * | 12/2006 | Gonnelli .................. A61M 5/30 239/1 |
| 7,931,614 | B2 | 4/2011 | Gonnelli et al. |
| 2002/0004639 | A1 | 1/2002 | Willis et al. |
| 2002/0151842 | A1 | 10/2002 | Gonnelli et al. |
| 2002/0156418 | A1 | 10/2002 | Gonnelli et al. |
| 2002/0161329 | A1 | 10/2002 | Gonnelli et al. |
| 2003/0135155 | A1 | 7/2003 | Alexandre et al. |
| 2003/0149397 | A9 | 8/2003 | Gonneiii et al. |
| 2004/0049151 | A1 | 3/2004 | Lell et al. |
| 2005/0010167 | A1 | 1/2005 | Alexandre et al. |
| 2005/0010168 | A1 | 1/2005 | Kendall |
| 2006/0258986 | A1 | 11/2006 | Hunter et al. |
| 2008/0262417 | A1 | 10/2008 | Kendall et al. |
| 2009/0326446 | A1 | 12/2009 | Alexandre |
| 2011/0172634 | A1 | 7/2011 | Gonnelli et al. |
| 2013/0237951 | A1 | 9/2013 | Oda |

FOREIGN PATENT DOCUMENTS

| | | | |
|---|---|---|---|
| JP | 2003-507134 | | 2/2003 |
| JP | 2003-534839 | | 11/2003 |
| JP | 2006-513765 | | 4/2006 |
| JP | 2006-122712 | | 5/2006 |
| JP | 2008-529677 | | 8/2008 |
| JP | 2008-220980 | | 9/2008 |
| JP | 2009-510322 | | 3/2009 |
| JP | 2009-543634 | | 12/2009 |
| JP | 2010-155060 | A | 7/2010 |
| JP | 2012-061269 | A | 3/2012 |
| JP | 2014-147841 | A | 8/2014 |
| WO | WO 01/13977 | A1 | 3/2001 |
| WO | WO 2004/075957 | A1 | 9/2004 |
| WO | WO 2006/086774 | A2 | 8/2006 |
| WO | WO 2007/034229 | A1 | 3/2007 |
| WO | WO 2009/065835 | A1 | 5/2009 |
| WO | WO 2010/065133 | A2 | 6/2010 |

OTHER PUBLICATIONS

Joy Schramm-Baxter, Samir Mitragotri, "Needle-free jet injections: dependence of jet penetration and dispersion in the skin on jet power", Journal of Controlled Release (U.S.A.) 97(2004), p527-535.
International Preliminary Report on Patentability in International Application No. PCT/JP2011/071211 dated Apr. 16, 2013.
Extended European Search Report for International Application No. PCT/JP2011/071211 dated Jan. 24, 2014 by European Patent Office.
Hungarian Search Report for corresponding Singapore Patent Application No. 201301930-2 dated Apr. 17, 2014 by Hungarian Intellectual Property Office.
Chinese Office Action received on Jul. 2, 2014 for corresponding Chinese Application No. 201180055451.X.
Japanese Office Action, dated Jan. 5, 2016, received in corresponding Japanese Patent Application No. 2014-096128.
International Search report, dated Nov. 1, 2011, received in corresponding International Patent Application No. PCT/JP2011/071211.
Final Decision of Rejection dated Apr. 10, 2018 in related Japanese Application No. 2016-198115.
Extended European Search Report dated Dec. 5, 2017 in related European Application No. 17185025.8.
Extended European Search Report dated Jan. 2, 2018 in related European Application No. 17185750.1.
Office Action dated Sep. 5, 2017 in corresponding Japanese Application No. 2016-198115.
Office Action dated Aug. 27, 2018 in corresponding Indian Application No. 2590/CHENP/2013.

* cited by examiner

SYRINGE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The following application is incorporated herein by reference in its entirety:

| Attorney Docket No. | Title | Application No. | Date Filed |
|---|---|---|---|
| TOYA193.002C2 | SYRINGE | 15/694,633 | Sep. 1, 2017 |

TECHNICAL FIELD

The present invention relates to a syringe (injector) with which an injection objective substance is injected into an injection target area of a living body without using any injection needle.

BACKGROUND ART

In relation to a needle-free syringe (needleless syringe) with which the injection is performed without using any injection needle, a construction is adopted in some cases such that an injection component is injected or allowed to inject by applying a pressure to an accommodating chamber in which an injection solution is accommodated, by means of a pressurized gas or a spring. However, in the case of the needle-free syringe having the conventionally known construction, the reproducibility is unsatisfactory in relation to the depth and the injection amount of the injection solution. Therefore, it is difficult to affirm that such a needle-free syringe generally comes into widespread use.

Accordingly, such a technique is disclosed that a propellant charge, which is composed of a mixture of two types of powders, i.e., a high speed combustion powder and a low speed combustion powder, is utilized to adjust the output pressure (injection pressure) for the injection solution in a plurality of levels or stages (see, for example, Patent Document 1). Specifically, the injection solution is firstly allowed to inject by applying a large force to a piston by the combustion of the high speed combustion powder. As a result, the injection solution penetrates through a skin of a human body or the like, and the injection solution is fed into the body. After that, a pressure is continuously applied to such an extent that the injection solution can be diffused in the skin by the combustion of the low speed combustion powder.

Patent Document 2 discloses such a technique that an injection solution is administered in two stages by using a needle-free syringe. In this technique, the injection solution is allowed to inject by applying a high pressure thereto so that the injection solution penetrates into the skin, and then the pressure, which is applied to the injection solution, is lowered so that it is contemplated to disperse the injection solution in the skin. Further, Patent Document 3 discloses such a technique that the injection pressure for an injection solution is adjusted by the intensity of the electric current by using a magnet and a coil. In this technique, the injection pressure is adjusted so that a high pressure is firstly applied in order that the injection solution penetrates through the skin, and then an approximately constant pressure is provided in order that the desired injection solution is fed or delivered.

The pressure, which is applied to the injection solution when the needle-free syringe is used, is variously adjusted not only for such a purpose that the injection solution is allowed to arrive at the interior of the skin but also for other purposes other than the above. For example, in Patent Document 4, such a description is found that the increase in the pressure applied to the injection solution is unfavorable after the penetration through the skin in order to mitigate the noise generated when the injection solution is allowed to inject by using a pressurized gas.

In this context, the target, for which the injection is performed by using the needle-free syringe, is the living body such as the human body or the like in many cases. Accordingly, a discussion is provided in relation to the behavior of an injected solution with respect to a gel agent generally used for an experiment and the skin of the living body (see, for example, Non-Patent Document 1). This discussion refers, for example, to a correlation between a depth of a hole formed by the injection and a hole depth having a maximum dispersion width, and a correlation between the Young's modulus of the skin and the hole depth. Further, Non-Patent Document 2 refers to a correlation between the dispersion width of an injection solution in the human skin and the nozzle diameter of a needle-free syringe.

PRECEDING TECHNICAL DOCUMENTS

Patent Documents

Patent Document 1: JP2003-534839;
Patent Document 2: U.S. Pat. No. 2,704,542;
Patent Document 3: United States Patent Publication No. 2006/0258986;
Patent Document 4: United States Patent Publication No. 2005/0010168.

Non-Patent Documents

Non-Patent Document 1: Joy Baxter, Samir Mitragotri, "Jet-induced skin puncture and its impact on needle-free jet injections: Experimental studies and a predictive model", Journal of Controlled Release (U.S.A.) 106 (2005), p 361-373;
Non-Patent Document 2: Joy Schramm-Baxter, Samir Mitragotri, "Needle-free jet injections: dependence of jet penetration and dispersion in the skin on jet power", Journal of Controlled Release (U.S.A.) 97 (2004), p 527-535.

SUMMARY OF THE INVENTION

Problem to be Solved by the Invention

When the injection is performed for the living body, the component which is contained in the injection solution and the depth in the injection target area of the living body into which the component is to be fed differ depending on the purpose of the injection. This is because the injection target area of the living body includes various structures such as skin, muscle, internal organs and the like, and the biological tissues, which constitute the structures, have different functions depending on the depths from the surface (surface on which the syringe is brought in contact with the structure when the injection is performed), and because it becomes difficult to appropriately exhibit the effect if the component contained in the injection solution does not arrive at the objective biological tissue.

For example, the human skin can be distinguished or classified into epidermis, dermis, and subcutaneous tissue (hypodermis) in a layered form from the surface side. Further, the epidermis can be distinguished or classified into horny cell layer and intradermis. In order that the respective layers perform the respective functions anatomically, the horny cell layer is composed of keratinocytes, the intradermis is composed of dendritic cells and pigment cells, the dermis is composed of fibroblasts and collagen cells, and the subcutaneous tissue is composed of subcutaneous fat and the like. When an injection solution is injected for a predetermined purpose, it is preferable that the predetermined component contained therein is precisely delivered, for example, to the objective tissue.

In order that the injection objective substance is efficiently injected without a leakage when the injection objective substance is injected into the injection target area of the living body, it is necessary that the pressure, which is applied to the injection objective substance, should be appropriately controlled from the start to the end of the injection. That is, if the injection speed (velocity) of the injection objective substance, which is brought about by the pressurization, is too slow, the substance is rebounded by the skin. To the contrary, if the injection speed (velocity) is too fast, then the injection depth can be secured in the injection target area, but the injection speed exceeds an injection speed which is adequate to diffuse the substance in the area. Therefore, it is considered that the injection objective substance is rebounded due to the excessive supply, and it is difficult to contemplate the appropriate diffusion thereof. Taking the foregoing problem into consideration, an object of the present invention is to provide a syringe which makes it possible to feed an injection objective substance into an objective injection target area of a living body without using any injection needle so that the injection objective substance can be widely diffused at a depth.

Solution for the Problem

In order to solve the problem as described above, the present invention adopts the following construction. That is, the pressure, which is applied to an injection objective substance in order to allow the injection objective substance to inject, is adjusted in accordance with pressurizing modes having mutually different characteristics in relation to a syringe for injecting the injection objective substance into an injection target area of a living body without using any injection needle. Owing to the different pressurizing modes, the injection objective substance can be fed into a biological tissue at a desired depth in the injection target area.

Specifically, the present invention provides a syringe for injecting an injection objective substance into an injection target area of a living body without using any injection needle; the syringe including an enclosing unit which encloses the injection objective substance; a pressurizing unit which pressurizes the injection objective substance enclosed in the enclosing unit; and a flow passage unit which defines a flow passage so that the injection objective substance, which is pressurized by the pressurizing unit, is allowed to discharge to the injection target area. The pressurizing unit generates a first pressurizing mode in which a pressure applied to the injection objective substance in the pressurizing unit is raised to a first peak pressure in order to allow the injection objective substance to penetrate through a surface of the injection target area, and then the pressure applied to the injection objective substance is lowered to a waiting pressure; and a second pressurizing mode in which the injection objective substance having the waiting pressure is pressurized so that the pressure applied to the injection objective substance is raised to a second peak pressure to inject a predetermined injection amount of the injection objective substance.

In the syringe according to the present invention, the injection objective substance, which is to be injected into the injection target area of the living body, is enclosed in the enclosing unit, and the pressure is applied to the injection objective substance enclosed in the enclosing unit. Thus, the movement of the injection objective substance is prompted. As a result, the injection objective substance is allowed to discharge to the injection target area while passing through the flow passage unit. The injection objective substance contains a component or ingredient which is expected to exhibit any efficacy at the inside of the injection target area. As described above, the pressure applied in the pressurizing unit is the driving source when the injection objective substance is allowed to inject. Therefore, any enclosing state of the injection objective substance in the enclosing unit or any physical form for the injection objective substance such as liquid, fluid in a gel form, powder, solid in a granular form in the enclosing unit is available as long as that the injection objective substance can be allowed to inject by being pressurized in the pressurizing unit.

For example, the injection objective substance may be a liquid or solid in a gel form, provided that the fluidity, which makes it possible to allow the injection objective substance to inject, is secured or guaranteed. Further, the component, which is to be fed into the injection target area of the living body, is contained in the injection objective substance. The component may exist in such a state that the component is dissolved in the injection objective substance, or the component may be in such a state that the component is simply mixed without being dissolved. For example, the component to be fed includes, for example, vaccine for enhancing antibody, protein for beauty, and cultured cells for regenerating hair. The injection objective substance is formed by containing the component in a liquid or a fluid in a gel form or the like so that the component as described above can be allowed to inject.

Further, as for the pressurizing source to pressurize the injection objective substance by the pressurizing unit, it is possible to utilize a variety of pressurizing sources, provided that the pressurizing forms or modes of the first pressurizing mode and the second pressurizing mode described above can be used. The pressurizing source is exemplified, for example, by those which utilize the elastic force brought about by a spring or the like, those which utilize the pressurized gas, those which utilize the combustion of any explosive charge, and those which utilize an electric actuator (for example, a motor, a piezoelectric element or the like) for effecting the pressurization.

In this construction, the injection objective substance can be adequately injected into the injection target area of the living body owing to the two pressurizing modes realized by the pressurizing unit. In other words, when the first pressurizing mode and the second pressurizing mode are adopted, then the injection objective substance is fed to the objective injection depth of the injection target area such as the skin structure or the like, and the injection objective substance is diffused. In the first pressurizing mode, the pressure applied to the injection objective substance is raised to the first peak pressure, and then the pressure is lowered to the waiting pressure. Accordingly, the injection objective substance firstly penetrates through the surface of the injection target area of the living body, and the injection objective substance advances in the depth direction of the area.

The injection energy of the injection objective substance is determined by the flow rate of the substance allowed to inject per unit time. Therefore, the larger the pressurizing speed (velocity) for the injection objective substance (amount of pressure increase per unit time) in the first pressurizing mode is, the deeper the injection depth brought about by the injection objective substance in the first pressurizing mode is. In the first pressurizing mode, the pressure increase is adjusted so that at least the pressure, which is required to penetrate through the surface of the injection target area, is applied to the injection objective substance.

In this context, the applicant assumes the following mechanism for the injection into the injection target area, of the injection objective substance allowed to inject. It is not intended that the present applicant is restricted by this mechanism. It is considered that any other invention, which provides the effect that is the same as or equivalent to the effect of the present application as a result of the execution of the pressure control with respect to the injection objective substance as described in the present application, belongs to the category of the present invention, even if the other invention follows any mechanism different from the mechanism.

When the injection objective substance is allowed to discharge to the injection target area, then the forward end of the flow (jet flow) of the pressurized injection objective substance allowed to discharge at the early stage cuts out the injection target area, and the cut fragments are lifted upwardly by the back flow. Accordingly, a hole is bored, and the forward end of the jet flow advances in the depth direction. As the forward end of the jet flow is deepened, the injection energy, which is possessed by the jet flow, is lost by the friction with the back flow. When the injection energy is lost by the back flow, and the ability to cut out the injection target area is lost, i.e., when the injection energy is balanced with the resistance energy of the back flow, then the advance of the hole depth is stopped.

When the jet flow is provided into the injection target area, the same amount of the back flow comes upwardly in the opposite direction in the hole. Therefore, it is necessary that the hole diameter should be secured in order to allow the back flow to flow therethrough. However, the biological tissue, which is the injection target area, intrinsically has the elasticity, and hence the biological tissue has such a tendency that the biological tissue is contracted or shrunk to decrease the hole diameter. The contractile force (shrinkage force) narrows the back flow passage (reduces the diameter). Therefore, when such a state is given that the contractile force is relatively large with respect to the jet flow, then the resistance, which is brought about by the back flow, is increased, and the injection energy possessed by the jet flow is balanced at a relatively shallow position.

Taking the foregoing mechanism into consideration, the present invention is considered as follows. That is, when the pressure, which is applied to the injection objective substance, is raised to the first peak pressure, and the pressure is thereafter lowered to the waiting pressure, then the elastic force, which is intrinsically possessed by the injection target area of the living body, is relatively large as compared with the jet flow at a part of the penetrating passage (forward end portion of the penetrating passage) of the injection objective substance formed to arrive at a certain injection depth. Therefore, it is considered that the diameter of the penetrating passage is reduced. In this situation, it is considered that the forward end portion of the injection objective substance that is subjected to the pressure reduction to the waiting pressure, is in such a state that the pressure (waiting pressure) applied to the injection objective substance is generally balanced with the pressure brought about by the back flow from the injection target area of the living body, at such a position that the injection target area of the living body, which is positioned at the forward end portion of the penetrating passage having the reduced diameter, is not reached. It is considered that when the diameter is reduced at the part of the penetrating passage as described above, the strength against the jet flow is raised as compared with any portion which is not subjected to the reduction of the diameter. The increase in the strength means that it is difficult to secure the back flow route when the pressurization is performed again in the second pressurizing mode. Therefore, even when the pressurization is performed again in accordance with the second pressurizing mode after the arrival at the waiting pressure, the jet flow does not reach the forward end of the penetrating passage, because the area, through which the back flow passes, is lost in the contracted or shrunk penetrating passage, wherein the pressurization is principally effected for the injection objective substance existing in the portion of the penetrating passage not subjected to the diameter reduction. Therefore, the permeation of the injection objective substance is facilitated in the direction in which the injection objective substance is spread in the injection area of the living body, rather than the penetrating passage is further elongated in the depth direction. Thus, the injection objective substance is diffused in a wide range. In a way, it is also affirmed that the first pressurizing mode, which is provided until arrival at the waiting pressure, is the step which makes it possible to form such a state that the diffusion is to be performed, and the second pressurizing mode is the step which accelerates the diffusion of the injection objective substance in the formed state. In the second pressurizing mode, the pressure applied to the injection objective substance is raised to the second peak pressure, and thus it is possible to realize the injection of the injection objective substance in an objective predetermined injection amount.

The first peak pressure and the waiting pressure in the first pressurizing mode described above and the second peak pressure in the second pressurizing mode are appropriately determined depending on the purpose of the injection of the injection objective substance. In this context, it is also appropriate to consider the physical property of the injection target area of the living body as the target, for example, the Young's modulus or the like of the skin. The living body, which is the injection target of the syringe according to the present invention, is not limited to human, which may be, for example, a farm animal such as pig or a pet such as dog.

As described above, according to the syringe according to the present invention, the injection objective substance undergoes the waiting pressure when the mode transitions from the first pressurizing mode to the second pressurizing mode. Thus, it is possible to effectively contemplate the diffusion of the injection objective substance in the injection target area without uselessly deepening the injection depth. That is, the syringe according to the present invention makes it possible to widely diffuse the injection objective substance at a relatively shallow depth in the injection target area of the living body.

In the syringe as described above, it is also preferable that the waiting pressure is not more than a first predetermined ratio of the first peak pressure. The present applicant found out the fact that the effective diffusion of the injection objective substance as described above can be realized when the ratio of the waiting pressure with respect to the first peak pressure is not more than the first predetermined ratio. Preferably, for example, the first predetermined ratio is set to 60%.

In the syringe as described above, it is also preferable that the second peak pressure is not more than the first peak pressure; and a pressure difference between the first peak pressure and the second peak pressure is within a second predetermined ratio with respect to the first peak pressure. That is, the second peak pressure is not more than the first peak pressure. However, the pressure difference therebetween is suppressed so that the pressure difference does not exceed the second predetermined ratio on the basis of the first peak pressure. Accordingly, it is possible to realize the injection in an objective injection amount in the second pressurizing mode without uselessly deepening the injection depth.

On the other hand, in the syringe as described above, it is also preferable that the second peak pressure is a pressure which exceeds the first peak pressure. In accordance with the mechanism assumed as described above, even when the second peak pressure exceeds the first peak pressure, then the effective diffusion of the injection objective substance is facilitated after the injection objective substance once arrives at the waiting pressure, and it is possible to suppress any useless increase in the injection depth. The injection with the desired amount is easily realized in the second pressurizing mode in some cases by raising the second peak pressure as described above depending on the physical property or characteristic of the injection target area of the living body.

In the syringe as described above, it is also preferable that a rate of pressure increase from the waiting pressure to the second peak pressure in the second pressurizing mode is set to be lower than a rate of pressure increase from start of pressurization to the first peak pressure in the first pressurizing mode. Accordingly, the pressure undergoes the waiting pressure in the first pressurizing mode, and thus it is possible to realize the effective diffusion of the injection objective substance.

It is also preferable that an amount of the injection objective substance in the second pressurizing mode is set to be larger than an amount of the injection objective substance in the first pressurizing mode. It is considered that most of the injection objective substance, which is allowed to inject in the first pressurizing mode until arrival at the waiting pressure, is subjected to the hole formation (boring) in the injection target area in order to form the state appropriate to diffuse the injection objective substance in the injection target area as described above, and the injection objective substance is generally discharged as the back flow to the outside of the injection target area. In view of the above, when the injection amount is relatively increased in the second pressurizing mode as described above, then a larger amount of the injection objective substance can be diffused to the objective depth of the injection target area, and it is expected to exhibit the effect of the component or ingredient contained in the injection objective substance.

In this context, in the syringe as described above, it is also preferable that the syringe further comprises an ignition device which includes an ignition charge; and a combustion chamber into which a combustion product produced by combustion of the ignition charge is allowed to flow and which accommodates a gas generating agent that is to be combusted by the combustion product to produce a predetermined gas; wherein the syringe is constructed so that a pressure in the combustion chamber is applied to the injection objective substance enclosed in the enclosing unit. Further, in this construction, the pressurizing unit uses an increase in pressure generated by the combustion of the ignition charge in the ignition device as a pressurization transition until arrival at the first peak pressure in the first pressurizing mode; and an increase in pressure brought about by the predetermined gas produced by the gas generating agent as a pressurization transition until arrival at the second peak pressure in the second pressurizing mode.

That is, the form or mode, in which the pressure produced by the combustion of the explosive charge is utilized as the driving source for allowing the injection objective substance to be discharged, can be adopted as a specified example in order to realize the pressurization applied to the injection objective substance in accordance with the first pressurizing mode and the second pressurizing mode as described above. In the case of the syringe constructed as described above, it is possible to preferably adjust the pressure transition in the first pressurizing mode and the pressure transition in the second pressurizing mode by appropriately adjusting the respective components of the gas generating agent and the ignition charge for the ignition device, the respective shapes in the syringe, and the relative arrangement relationship therebetween. The exemplary description of the driving source based on the use of the explosive charge as described above does not include any intention to exclude the adoption of any driving source based on any other form or mode. For example, it is also allowable to adopt, as the driving source as described above, those which utilize the elastic force brought about by a spring or the like, those which utilize the pressurized gas, and those which utilize an electric actuator (for example, a motor, a piezoelectric element or the like) in order to effect the pressurization.

In the syringe as described above, it is also preferable that a decrease in pressure, which is brought about by condensation of the combustion product in the combustion chamber in the first pressurizing mode, is used as a depressurization transition from the first peak pressure to the waiting pressure. The condensation action of the combustion product is utilized for the decrease in pressure, and thus it is possible to suppress the kinetic energy possessed by the injection objective substance until arrival at the waiting pressure, while maintaining the energy for penetrating through the surface of the injection target area of the living body. It is possible to perform the injection at a shallower portion of the injection target area of the living body.

In the syringe as described above, it is also preferable that a combustion completion time of the ignition charge comes earlier than a combustion completion time of the gas generating agent; and a velocity of production of the gas from the gas generating agent is increased at a stage at which the combustion of the ignition charge is completed and the pressure applied to the injection objective substance is decreased from the first peak pressure to the waiting pressure. That is, it is also allowable that the combustion period of the ignition charge and the combustion period of the gas generating agent are partially overlapped with each other, provided that the waiting pressure can be secured in the first pressurizing mode described above. When the combustion periods are overlapped, then the pressure brought about by the combustion of the ignition charge is superimposed on the pressure of the produced gas produced from the gas generating agent, and the resultant pressure is applied to the injection objective substance. In order to adjust the combustion completion times of the ignition charge and the gas generating agent as described above, it is possible to change the respective compositions and the composition ratios. Even when the both have the same composition and the composition ratio, it is also allowable to change the respective shapes and dimensions (sizes). For example, when the state of the explosive charge is powdery, the combustion completion time comes earlier than the combustion completion time of an explosive charge having the same composition formed in a form of lump. Further, the combustion completion time can be also adjusted by changing both of the composition and the shape and the dimension (size). In this way, even when the explosive charges having the same composition are contained in the ignition charge and the gas generating agent, it is possible to adjust the respective combustion completion times by adjusting, for example, the state, the shape, and the dimension (size) of each of the explosive charges.

In the syringe as described above, it is also preferable that the ignition charge is any one of explosive charges of an explosive charge containing zirconium and potassium perchlorate, an explosive charge containing titanium hydride and potassium perchlorate, an explosive charge containing titanium and potassium perchlorate, an explosive charge containing aluminum and potassium perchlorate, an explosive charge containing aluminum and bismuth oxide, an explosive charge containing aluminum and molybdenum oxide, an explosive charge containing aluminum and copper oxide, and an explosive charge containing aluminum and iron oxide, or an explosive charge composed of a combination of a plurality of the foregoing explosive charges. The ignition charges as described above have the following feature. That is, the combustion product does not contain any gas component at the ordinary temperature even when any gas is produced in a high temperature state. Therefore, when the combustion product is brought in contact with the surface in the combustion chamber, the condensation occurs immediately. Therefore, it is possible to perform the injection at a shallower portion of the injection target area of the living body.

Effect of the Invention

It is possible to feed the injection objective substance to the depth of the objective injection target area of the living body without using any injection needle so that the injection objective substance can be widely diffused at the depth brought about thereby.

MODE FOR CARRYING OUT THE INVENTION

Figure 1:
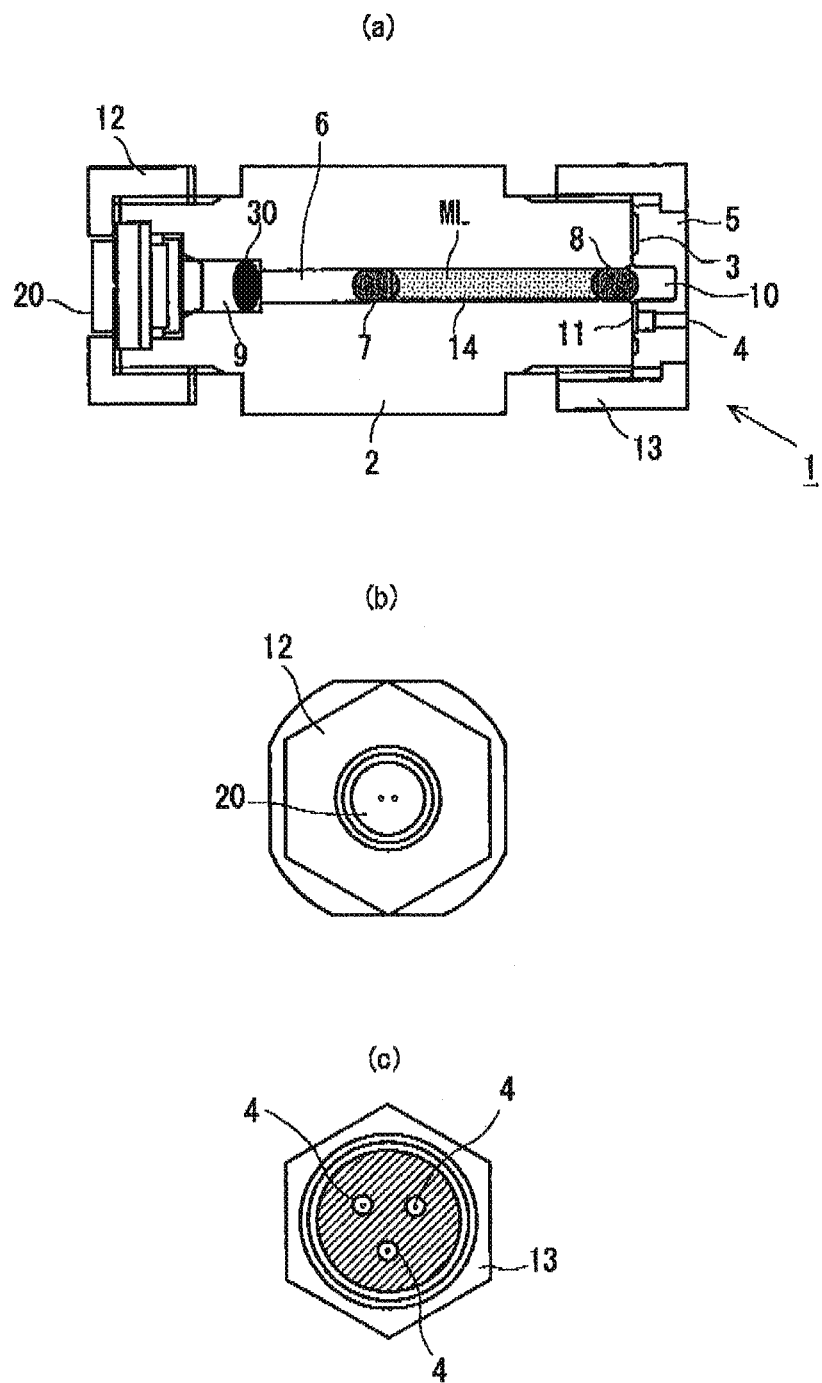
FIG. 1 shows a schematic arrangement of a syringe according to the present invention.

A syringe 1 according to an embodiment of the present invention will be explained below with reference to the drawings. The construction of the following embodiment is described by way of example. The present invention is not limited to the construction of the embodiment.

In this embodiment, FIG. 1(a) shows a sectional view illustrating the syringe 1, FIG. 1(b) shows a side view illustrating the syringe 1 as viewed from a side of an initiator 20, and FIG. 1(c) shows a side view illustrating the syringe 1 as viewed from a side of nozzles 4 for allowing an injection solution to inject. The syringe 1 has a main syringe body 2. A through-hole 14, which extends in the axial direction and which has a constant diameter in the axial direction, is provided at a central portion of the main syringe body 2. One end of the through-hole 14 is communicated with a combustion chamber 9 which has a diameter that is larger than the diameter of the through-hole 14. The remaining other end reaches the side of a nozzle hole 5 in which the nozzles 4 are formed. Further, the initiator 20 is installed on the side opposite to the communicated portion of the combustion chamber 9 communicated with the through-hole 14 so that the ignition unit thereof is opposed to the communicated portion.

Figure 2:
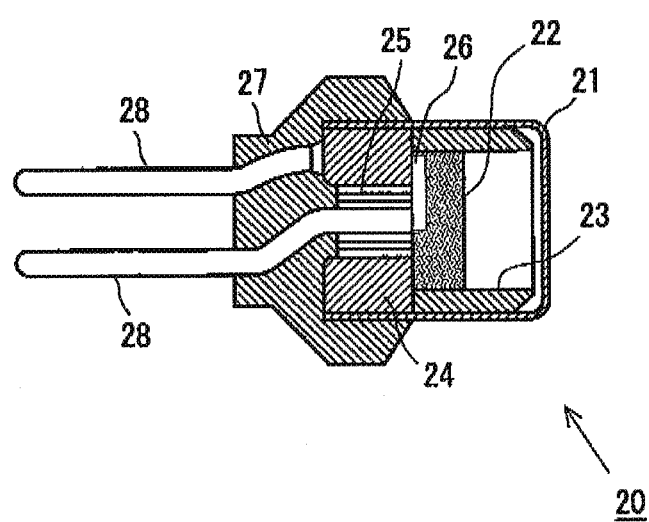
FIG. 2 shows a schematic arrangement of an initiator (ignition device) installed to the syringe shown in FIG. 1.

An example of the initiator 20 will now be explained on the basis of FIG. 2. The initiator 20 is an electric ignition device. A space for arranging an ignition charge 22 is defined in a cup 21 by the cup 21 having a surface covered with an insulating cover. A metal header 24 is arranged in the space, and a cylindrical charge holder 23 is provided on an upper surface thereof. The ignition charge 22 is held by the charge holder 23. A bridge wire 26, which electrically connects one conductive pin 28 and the metal header 24, is wired at the bottom portion of the ignition charge 22. Two conductive pins 28 are fixed to the metal header 24 with an insulator 25 intervening therebetween so that they are in a mutually insulated state when no voltage is applied. Further, an opening of the cup 21, from which the two conductive pins 28 supported by the insulator 25 extend, is protected by a resin 27 in a state in which the insulation performance is maintained to be satisfactory between the two conductive pins 28.

In the initiator 20 constructed as described above, when the voltage is applied between the two conductive pins 28 by an external power source, then the current flows through the bridge wire 26, and the ignition charge 22 is combusted thereby. In this situation, the combustion product, which is produced by the combustion of the ignition charge 22, is spouted from the opening of the charge holder 23. Accordingly, in the present invention, the relative positional relationship of the initiator 20 with respect to the main syringe body 2 is designed so that the combustion product of the ignition charge 22, which is produced in the initiator 20, flows into the combustion chamber 9. Further, an initiator cap 12 is formed to have a brim-shaped cross section so that the initiator cap 12 is hooked by the outer surface of the initiator 20, and the initiator cap 12 is screw-fixed to the main syringe body 2. Accordingly, the initiator 20 is fixed to the main syringe body 2 by means of the initiator cap 12. Thus, the initiator 20 itself can be prevented from being disengaged from the main syringe body 2, which would be otherwise disengaged by the pressure brought about upon the ignition in the initiator 20.

The ignition charge 22, which is used for the syringe 1, is preferably exemplified by an explosive charge (ZPP) containing zirconium and potassium perchlorate, an explosive charge (THPP) containing titanium hydride and potassium perchlorate, an explosive charge (TiPP) containing titanium and potassium perchlorate, an explosive charge (APP) containing aluminum and potassium perchlorate, an explosive charge (ABO) containing aluminum and bismuth oxide, an explosive charge (AMO) containing aluminum and molybdenum oxide, an explosive charge (ACO) containing aluminum and copper oxide, and an explosive charge (AFO) containing aluminum and iron oxide, or an explosive charge composed of a combination of a plurality of the foregoing explosive charges. The explosive charges as described above exhibit such a characteristic that the plasma having a high temperature and a high pressure is generated during the combustion immediately after the ignition, but the generated pressure is suddenly lowered because no gas component is contained when the ordinary temperature is given and the combustion product is condensed. This characteristic is the characteristic which preferably contributes to the formation of the pressurizing mode for the injection solution in the syringe 1 according to the present invention, and this feature will be described later on. Any explosive charge other than the above may be used as the ignition charge provided that the pressurizing mode can be realized as described later on.

In this embodiment, a gas generating agent 30 having a columnar shape, which is combusted by the combustion product produced by the combustion of the ignition charge 22 to produce the gas, is arranged in the combustion chamber 9. The gas generating agent 30 is exemplified, for example, by a single base smokeless propellant composed of 98% by mass of nitrocellulose, 0.8% by mass of diphenylamine, and 1.2% by mass of potassium sulfate by way of example. It is also possible to use various gas generating agents used for a gas generator for an airbag and a gas generator for a seat belt pretensioner. Unlike the ignition charge 22 described above, in the case of the gas generating agent 30, the predetermined gas, which is produced during the combustion, contains the gas component even at the ordinary temperature. Therefore, the rate of decrease in the generated pressure is extremely small as compared with the ignition charge 22 described above. Further, the combustion completion time upon the combustion of the gas generating agent 30 is extremely long as compared with the ignition charge 22 described above. However, it is possible to change the combustion completion time of the gas generating agent 30 by adjusting the dimension, the size, and/or the shape, especially the surface shape of the gas generating agent 30 when the gas generating agent 30 is arranged in the combustion chamber 9. This is because the contact state, which is provided with respect to the combustion product of the ignition charge 22 allowed to flow into the combustion chamber 9, is considered to be changed depending on the surface shape of the gas generating agent 30 and the relative positional relationship between the gas generating agent 30 and the ignition charge 22 resulting from the arrangement of the gas generating agent 30 in the combustion chamber 9.

In the next place, a piston 6 made of metal is arranged in the through-hole 14 so that the piston 6 is slidable in the axial direction in the through-hole 14. One end thereof is exposed to the side of the combustion chamber 9, and a sealing member 7 is integrally attached to the other end. An injection solution ML, which is the injection objective substance to be injected from the syringe 1, is enclosed in a space formed in the through-hole 14 between the sealing member 7 and another sealing member 8. Therefore, the enclosing unit of the syringe according to the present invention is formed by the sealing members 7, 8 and the through-hole 14. Each of the sealing members 7, 8 is made of rubber having the surface thinly coated with silicon oil so that the injection solution does not leak when the injection solution ML is enclosed, and the injection solution ML can be smoothly moved in the through-hole 14 in accordance with the sliding movement of the piston 6.

In this embodiment, a flow passage unit of the syringe 1 according to the present invention is formed on the forward end side of the syringe 1 (right side as viewed in FIG. 1). Specifically, a holder 5, which is formed with nozzles 4 for allowing the injection solution ML to inject, is provided on the forward end side of the syringe 1. The holder 5 is fixed to the end surface of the main syringe body 2 with a gasket 3 intervening therebetween by the aid of a holder cap 13. The holder cap 13 is formed to have a brim-shaped cross section so that the holder cap 13 fixes the holder 5, and the holder cap 13 is screw-fixed to the main syringe body 2. Accordingly, the holder 5 is prevented from being disengaged from the main syringe body 2 by the pressure applied to the injection solution ML when the injection solution ML is allowed to inject.

A recess 10, which can accommodate the sealing member 8, is formed at a portion opposed to the sealing member 8 in a state in which the holder 5 is attached to the main syringe body 2. The recess 10 has approximately the same diameter as that of the sealing member 8, and the recess 10 has a depth which is slightly longer than the length of the sealing member 8. Accordingly, when the pressure is applied to the piston 6, and the injection solution ML is moved to the forward end side of the syringe 1 together with the sealing members 7, 8, then the sealing member 8 can be accommodated in the recess 10. When the sealing member 8 is accommodated in the recess 10, the pressurized injection solution ML is released. Thus, a flow passage 11 is formed at a portion of the holder 5 brought in contact with the side of the main syringe body 2 so that the released injection solution ML is guided to the nozzle 4. Accordingly, the released injection solution ML passes through the flow passage 11, and the injection solution ML is allowed to discharge from the nozzle 4 to the injection target. Owing to the fact that the recess 10 has the depth for accommodating the sealing member 8, any inhibition of the injection of the injection solution ML, which would be otherwise caused by the sealing member 8, can be avoided.

A plurality of nozzles 4 may be formed for the holder 5. Alternatively, one nozzle 4 may be formed. When the plurality of nozzles is formed, the flow passages, which correspond to the respective nozzles, are formed so that the released injection solution is fed to the respective nozzles. Further, when the plurality of nozzles 4 is formed, as shown in FIG. 1(*c*), it is preferable that the respective nozzles are arranged at equal intervals around the central axis of the syringe 1. In this embodiment, the three nozzles 4, which are provided for the holder 5, are arranged at equal intervals around the central axis of the syringe 1. The diameter of the nozzle 4 is appropriately set while considering, for example, the injection target, the injection pressure applied to the injection solution ML, and the physical property (viscosity) of the injection solution.

In the syringe 1 constructed as described above, the combustion product or the predetermined gas is generated in the combustion chamber 9 by means of the ignition charge 22 provided in the initiator 20 and the gas generating agent 30 arranged in the combustion chamber 9 so that the pressure is applied to the injection solution ML enclosed in the through-hole 14 by the aid of the piston 6. As a result, the injection solution ML is pushed or extruded to the forward end side of the syringe 1 together with the sealing members 7, 8. When the sealing member 8 is accommodated in the recess 10, then the injection solution ML passes through the flow passage 11 and the nozzles 4, and the injection solution ML is allowed to inject to the injection target. The pressure is applied to the injection solution ML allowed to inject. Therefore, the injection solution ML penetrates through the surface of the injection target, and the injection solution ML arrives at the inside thereof. Accordingly, it is possible to achieve the purpose of the injection with the syringe 1.

Figure 3:
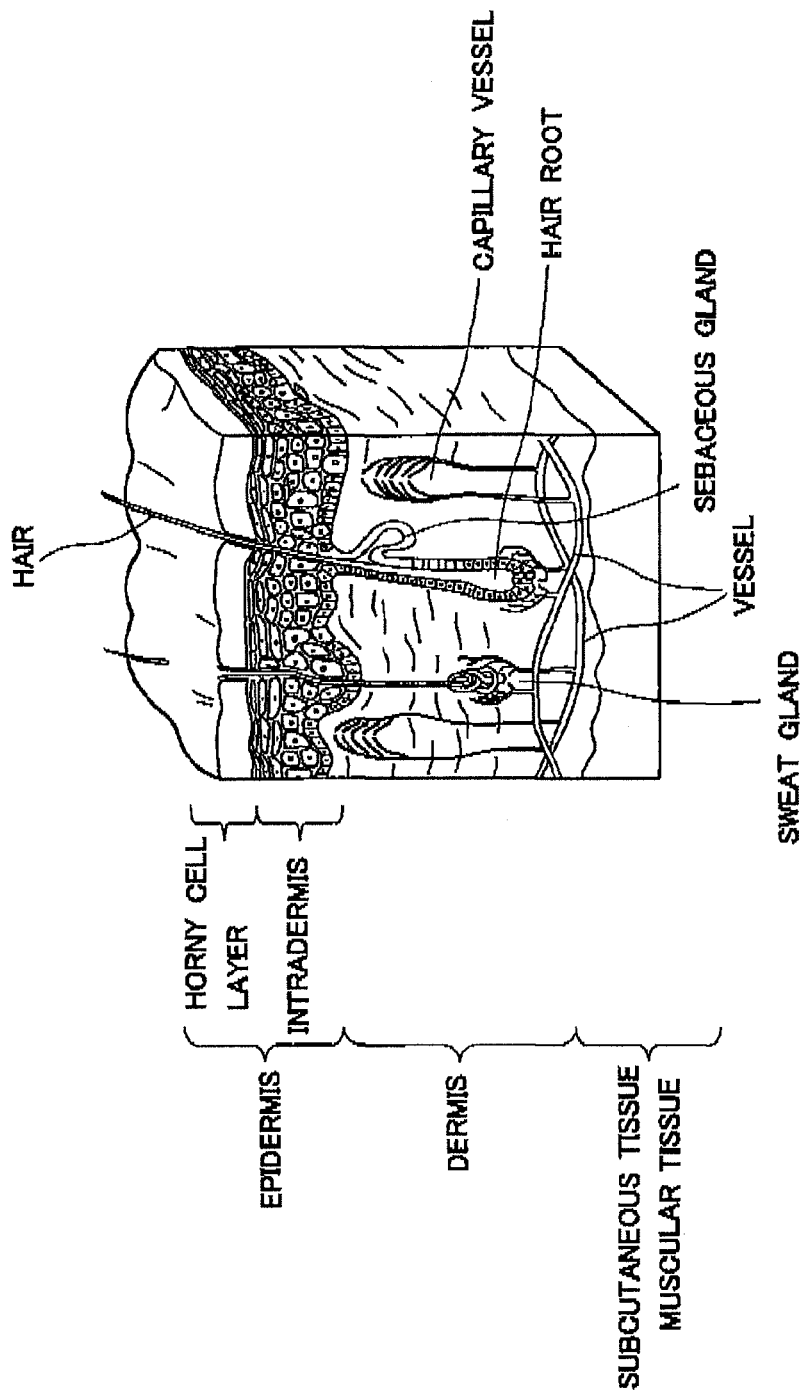
FIG. 3 schematically shows the skin structure of human.

In this embodiment, the injection target of the syringe 1 according to the present invention is the skin structure of the living body such as human, farm animal or the like. This specification principally refers to the action of the syringe 1 exerted on the human skin. Therefore, FIG. 3 schematically shows an anatomical structure of the human skin. The human skin is constructed in a layered form including epidermis, dermis, subcutaneous tissue (hypodermis), and muscular tissue as disposed in the depth direction from the side of the skin surface. Further, the epidermis can be distinguished or classified into horny cell layer and intradermis in a layered form. In each of the layers of the skin structure, the tissue and the main cells or the like for constructing the tissue have different features as well.

Specifically, the horny cell layer is principally composed of keratinocytes, and the horny cell layer is positioned on the outermost surface side of the skin. Therefore, the horny cell layer has the function of the so-called barrier layer. In general, the thickness of the horny cell layer is about 0.01 to 0.015 mm, and the horny cell layer performs the surface protection for human by keratinocytes. Therefore, in order to physically insulate the interior of the human body from the external environment to some extent, a relatively high strength is required as well. On the other hand, the intradermis is constructed to include dendritic cells (Langerhans cells) and pigment cells (melanocytes). The epidermis is formed by the horny cell layer and the intradermis. The thickness of the epidermis is generally about 0.1 to 2 mm. It is considered that the dendritic cells in the intradermis are cells which participate in the antigen-antibody reaction. This is because the dendritic cells recognize the presence of the antigen by incorporating the antigen, and the antigen-antibody reaction, in which lymphocytes are activated to play a role to attach the foreign matter, tends to be induced. On the other hand, the pigment cells in the intradermis have the function to avoid the influence of the ultraviolet light radiated from the external environment.

In the next place, vessels and capillary vessels on the skin are complicatedly spread all over the dermis. Further, for example, sweat glands for adjusting the body temperature, hair roots of body hair (including hair on the head), and sebaceous glands associated therewith also exist in the dermis. The dermis is the layer which makes communication between the epidermis and the interior of the human body (subcutaneous tissue and muscular tissue). The dermis is constructed to include fibroblasts and collagen cells. Therefore, the state of the dermis greatly participates, for example, in the hair falling out and the appearance of wrinkles due to the so-called collagen shortage or the elastin shortage.

In this way, the skin structure of human is generally formed in the layered form. The intrinsic anatomical function is exhibited, for example, by the cells and the tissue principally contained in each of the layers. This means the fact that it is desirable to inject a component (ingredient) for a medical treatment to a place (depth) of the skin structure in conformity with the purpose of the medical treatment, for example, when the medical treatment is applied to the skin. For example, the dendritic cells exist in the intradermis. Therefore, when a vaccine injection is performed therein, it is possible to expect a more effective antigen-antibody reaction. However, in the case of the conventional injection technique, it is difficult to perform the vaccine injection with respect to the intradermis which is positioned at the relatively shallow portion. Even when such a vaccine injection is performed, the injection greatly depends on the skill of a health care worker or medical professional. Further, the pigment cells exist in the intradermis, and hence it is also demanded that when a beauty treatment is performed for the so-called skin whitening, a specified component (ingredient) for the skin whitening is injected into the intradermis. However, in the case of the conventional technique, it is difficult to perform such a treatment as described above.

In the next place, fibroblasts and collagen cells exist in the dermis. Therefore, for example, if protein for removing skin wrinkles, enzyme, vitamin, amino acid, mineral, sugar, nucleic acid, and various growth factors (epithelial cells and fibroblasts) are injected into the dermis, an effective beauty treatment effect is expected. However, the dermis is also positioned at the relatively shallow portion in the same manner as the intradermis. Therefore, in the case of the conventional technique, it is difficult to perform the beauty treatment by means of the injection in many cases. As for a hair regeneration treatment, the hair roots are positioned in the dermis. Therefore, in order to perform the hair regeneration treatment, the following procedure is considered to be favorable. That is, for example, a stem cell injection method, in which dermal papilla cells and/or epidermal stem cells are autologous cultured and cultured cells are autologous transplanted to the scalp, is performed, or several types of growth factors and/or nutrient components extracted from stem cells are injected into a portion positioned in the vicinity of the dermis.

In this way, the substance, which is injected in accordance with the purpose of the treatment for the skin, individually corresponds to the position (depth) in the skin structure into which the substance is desirably injected. However, it is difficult for the conventional technique to adjust the injection position. In the case of the syringe 1 according to the present invention, the depth, at which the injection solution arrives in the skin structure, can be preferably adjusted by adjusting the pressure applied to the injection solution. As described above, various substances (injection objective substances) are used to be injected into the skin structure depending on the purpose of the treatment thereof. Therefore, the injection objective substance is generally referred to as "injection solution" in the following description. However, this includes no intention to limit the form and the contents of the substance to be injected. As for the injection objective substance, the component (ingredient), which is to be delivered to the skin structure, may be either dissolved or not dissolved. Any specified form is also available for the injection objective substance provided that the injection objective substance can be allowed to inject to the skin structure from the nozzle 4 by being pressurized. It is possible to adopt various forms including, for example, liquid and gel forms.

For example, the injection objective substance usable in the beauty treatment is exemplified, for example, by protein for skin whitening or for removing wrinkles, enzyme, vitamin, amino acid, mineral, sugar, nucleic acid, and various growth factors (epithelial cells and fibroblasts). Further, the injection objective substance in the hair regeneration treatment is exemplified, for example, by dermal papilla cell, hair root stem cell, epidermal stem cell, HARG cocktail, and hair for transplantation.

Figure 4:
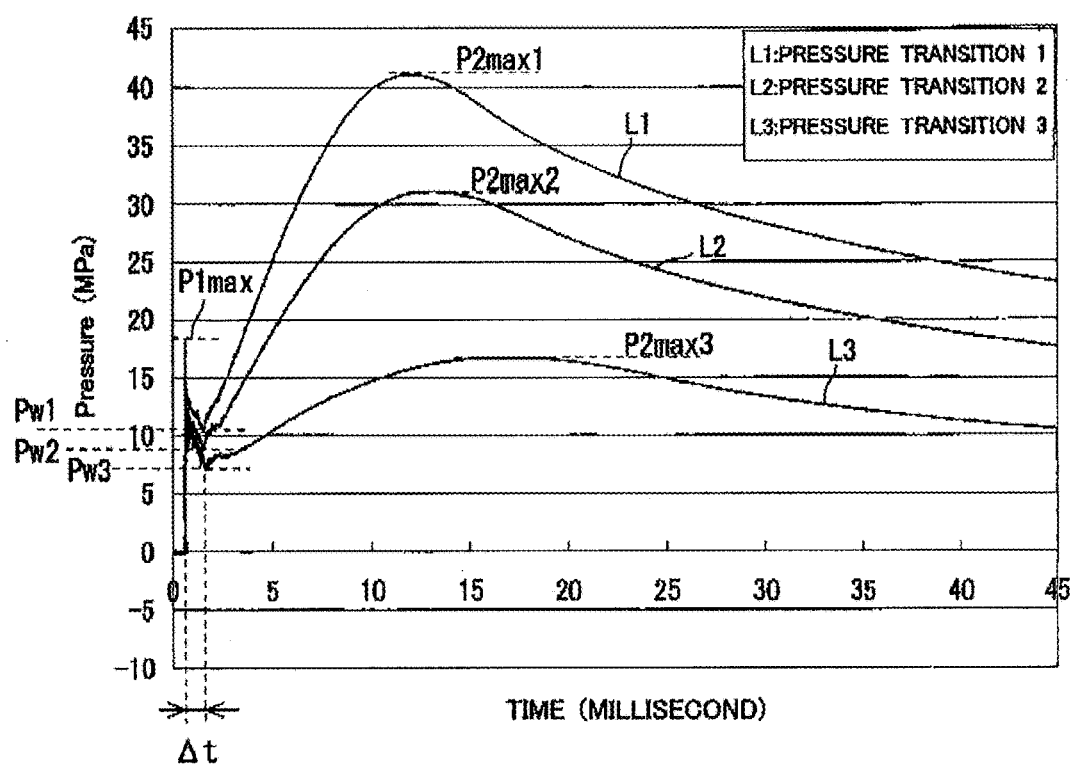
FIG. 4 shows the transition of the pressure applied to the injection solution in the syringe shown in FIG. 1.

In the next place, an explanation will be made on the basis of FIG. 4 about the specified pressurizing form for the injection solution as performed in the syringe 1. FIG. 4 shows the pressure transition applied to the injection solution enclosed in the through-hole 14 by the aid of the piston 6 by appropriately adjusting the combination of the ignition charge 22 and the gas generating agent 30 contained in the syringe 1. The horizontal axis of FIG. 4 represents the elapsed time in millisecond, and the vertical axis represents the applied pressure in MPa. The pressure can be measured by installing a pressure gauge in a pressure measuring port (not shown in FIG. 1) provided to make communication with the combustion chamber 9 in the main syringe body 2. In the example shown in FIG. 4, the pressure transitions, which are provided when three types of amounts of the gas generating agent 30 are combined with the same amount of ZPP (containing zirconium and potassium perchlorate) as the ignition charge 22, are shown as L1, L2, L3 in FIG. 4.

An explanation will now be made about the pressure transitions L1 to L3 in the syringe 1 according to the present invention. The pressure transitions involve the common technical feature. At first, the common technical feature will be explained on the basis of the pressure transition L2. In the pressure transition in the present invention, the combustion of the ignition charge 22 is started immediately after the application of the electricity to the initiator 20, and thus the pressure suddenly arrives at the first peak pressure value P1max from the state in which the pressure is zero. After that, the pressure is lowered to the waiting pressure Pw2 (the waiting pressure is represented by Pw1 in the pressure transition L1, and the waiting pressure is represented by the waiting pressure Pw3 in the pressure transition L3). The process, in which the pressure is applied to the injection solution in accordance with the pressure transition as provided until arrival at this point, is referred to as "first pressurizing mode". After that, the pressure is raised again, and the pressure arrives at the second peak pressure P2max2 (the second peak pressure is represented by P2max1 in the pressure transition L1, and the second peak pressure is represented by P2max3 in the pressure transition L3). After that, the pressure is gently lowered. The process or step, in which the pressure is applied to the injection solution in accordance with the pressure transition for raising the pressure from the waiting pressure to the second peak pressure, is referred to as "second pressurizing mode". In this way, each of the pressure transitions L1 to L3 is constructed by the first pressurizing mode and the second pressurizing mode.

The two different pressurizing modes, which are provided in one pressure transition as described above, are realized by the ignition charge 22 and the gas generating agent 30 which have the different combustion modes or forms. That is, the feature of the combustion form of the ignition charge 22 resides in the instantaneous combustion brought about by the application of the electricity to the initiator 20. Further, when the produced combustion gas is condensed at the ordinary temperature, no gas component is contained therein, as represented by ZPP. Therefore, the pressure, which is applied to the injection solution, is suddenly lowered. Therefore, the pressure transition, which is based on the first pressurizing mode, is completed in a minute time Δt shown in FIG. 4. On the other hand, the combustion product having the high temperature, which is produced by the combustion of the ignition charge 22, flows into the combustion chamber 9, and the gas generating agent 30 arranged therein is combusted thereby. Accordingly, the combustion of the gas generating agent 30 is started. Therefore, the gas generating agent 30 is combusted during the pressure transition based on the first pressurizing mode or immediately after the completion of the first pressurizing mode, and the predetermined gas is produced thereby. The velocity of the generation of the gas from the gas generating agent 30 is extremely gentle as compared with the velocity of the generation of the combustion product from the ignition charge 22. In other words, the combustion completion time of the gas generating agent 30 is longer than the combustion completion time of the ignition charge 22. Therefore, as clarified from FIG. 4 as well, the pressure transition is depicted such that the pressure increase rate, which is provided from the waiting pressure Pw2 until arrival at the second peak pressure P2max2, is gentler than the pressure increase rate which is provided upon the ignition of the ignition charge 22. This feature is provided in the same manner for the pressure transitions L1, L3 as well.

Figure 5:
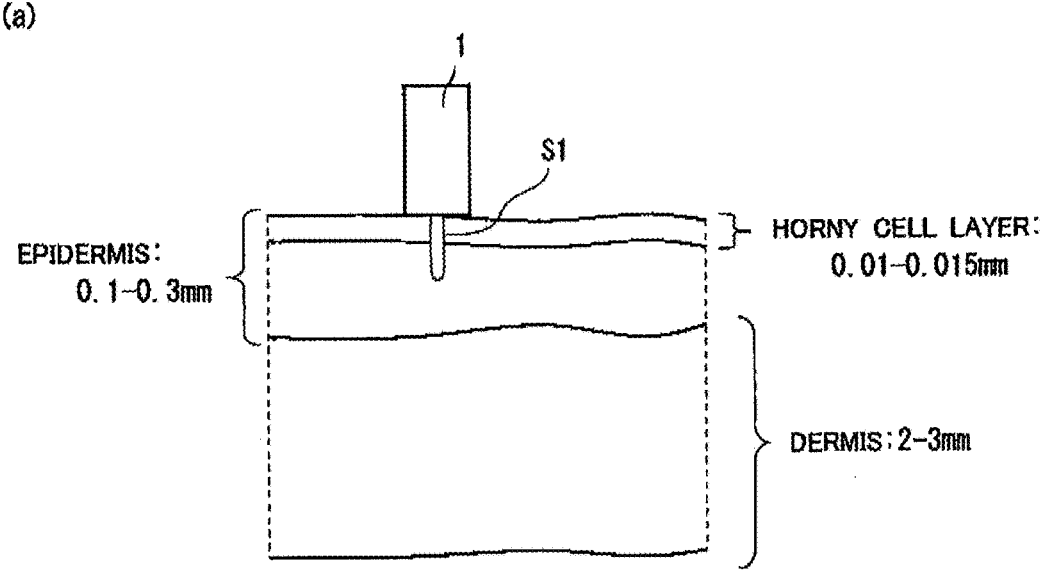
FIG. 5 shows a situation in which the injection solution is diffused in the skin structure of human when the pressure, which is in the transition as shown in FIG. 4, is applied to the injection solution.
Figure 5:
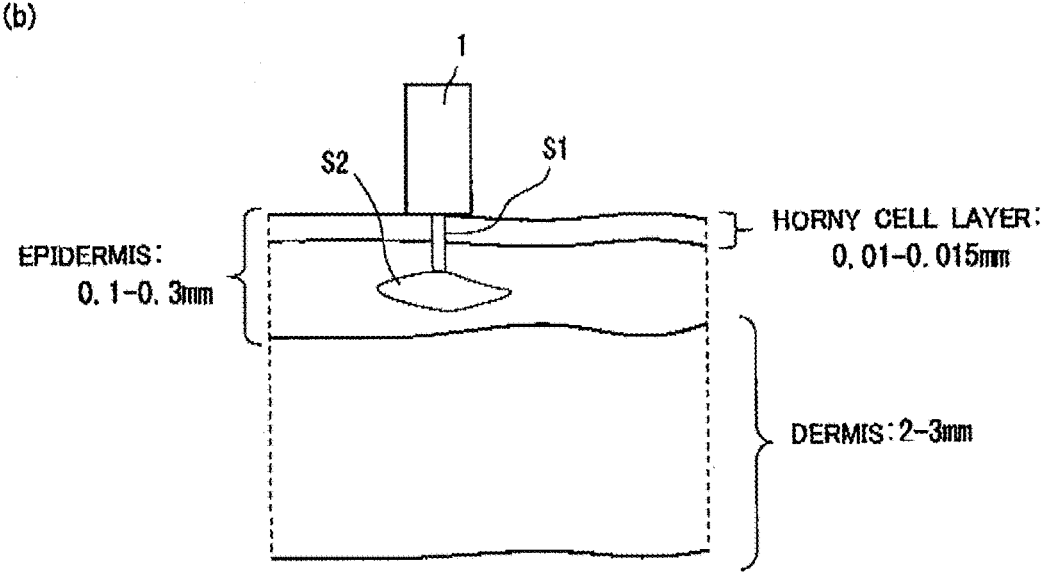

An explanation will be made on the basis of FIG. 5 about the conceptual injection situation of the injection solution in the human skin structure in accordance with the pressure transition based on the two pressurizing modes as described above. In the first pressurizing mode performed in the minute time Δt (time ranging from the application of electricity in the initiator 20 to the arrival at the waiting pressure Pw2), as shown in FIG. 5(a), a minute amount of the injection solution is allowed to inject from the syringe 1. In the injection of the minute amount of the injection solution, the energy amount, which is possessed by the injection solution allowed to inject depending on the injection amount per unit time, i.e., the injection flow rate, is determined by Expression 1 as follows.

$$P = \tfrac{1}{8} \cdot \pi \rho D^2 u^3 \qquad \text{(Expression 1)}$$

P: energy of discharging injection solution, ρ: density of injection solution, D: diameter of nozzle 4, u: discharging velocity of injection solution.

It is noted that Expression 1 merely calculates the energy amount possessed by the injection solution allowed to inject. Even when only Expression 1 is provided, it is insufficient to explain the adjustment of the injection depth in the skin structure. That is, in order to adjust the injection depth, it is necessary to perform the pressure control according to the present invention. In view of the above, an explanation will be made below about the pressure control according to the present invention in relation to the adjustment of the injection depth in the skin structure while taking Expression 1 into consideration.

In the first pressurizing mode, the pressure transition, in which the pressure arrives at the waiting pressure via the peak pressure P1max from zero, is performed in the extremely short period of time. Therefore, it is also affirmed that the injection solution having the high energy is allowed to inject to the skin in this process. As a result, the injection solution, which is allowed to inject in the first pressurizing mode, penetrates through the outermost surface of the skin, and the injection solution erodes the inside of the skin (discharging injection solution is represented by S1 in FIG. 5(a)). In this situation, it is considered that the injection depth is more deepened as the energy of the discharging injection solution in the first pressurizing mode represented by Expression 1 is more increased. In this context, according to Expression 1, the energy P of the discharging injection solution is proportional to the product of the cube of the discharging velocity u of the injection solution and the density of the injection solution. Therefore, the larger the peak pressure P1max is, the larger the energy P of the discharging injection solution is. Further, the shorter the minute time Δt for the execution of the first pressurizing mode is, the smaller the energy P is. Therefore, the injection depth, at which the injection solution can arrive in the skin, can be adjusted by adjusting the energy P. FIG. 5(a) schematically shows the situation in which the injection solution arrives at the layer portion of the epidermis in the human skin structure. However, when the energy amount is adjusted, then the injection depth can be made deeper in the first pressurizing mode, or the injection depth can be made shallower.

In this context, the waiting pressure, at which the pressure arrives in the first pressurizing mode, is such a pressure that the erosion, which is caused by the discharging injection solution in the first pressurizing mode in the injection depth direction at the inside of the skin structure, is mitigated, and the diameter of the penetrating passage can be reduced or shrunk at a part of the penetrating passage for the injection solution formed in the skin structure. In this case, when the pressure is raised to the peak pressure P1max and the pressure is thereafter lowered to the waiting pressure, then the energy amount possessed by the injection solution is lowered. Therefore, the erosion of the skin caused by the injection solution is mitigated, and the discharging injection solution does not arrive at the deepest portion of the skin structure. Further, the skin structure of the living body has a certain elastic force. Therefore, on account of the elastic force, the diameter of the penetrating passage may be reduced or contracted by the elastic force while including the injection solution or scarcely including the injection solution at a part of the penetrating passage having been already formed, especially on the forward end side (deep side in the depth direction). As a result, the state, in which the diameter is reduced, is formed on the forward end side of the penetrating passage, and the state, in which the diameter is not reduced, is maintained on the proximal end side of the penetrating passage, at the point in time at which the pressure arrives at the waiting pressure in the first pressurizing mode. Therefore, the difference in strength with respect to the pressure of the injection solution is generated between the forward end side and the proximal end side of the penetrating passage. That is, the strength is relatively high on the forward end side of the penetrating passage as compared with the proximal end side thereof. As a result, when the pressurization is performed again in the second pressurizing mode as described later on, then the pressure of the injection solution is uniformly applied to the entire penetrating passage, but the penetrating passage portion, which is in the unreduced diameter state, has the strength weaker than that of the reduced diameter portion, because the penetrating passage portion in the unreduced diameter state is relatively enlarged or expanded. It is considered that this situation contributes to the diffusion of the injection solution. According to the above, it is desirable that the waiting pressure is the pressure which is lowered from the peak pressure P1max in the first pressurizing mode to such an extent that the forward end side of the penetrating passage is contracted or shrunk by the elastic force exerted from the skin structure in the second pressurizing mode as described later on, i.e., to such an extent that the difference in strength of the penetrating passage, which can secure or guarantee the diffusion of the injection solution in accordance with the second pressurizing mode, is generated. For example, it is preferable that the waiting pressure is not more than 50% of the peak pressure P1max.

In the next place, the pressure transition, in which the pressure is raised from the waiting pressure Pw2 to the second peak pressure P2max2, is depicted in the second pressurizing mode. When the pressure of the injection solution is raised again in accordance with the second pressurizing mode from the state in which it is estimated that the difference in strength is generated in the penetrating passage formed by the injection solution owing to the arrival of the pressure of the injection solution at the waiting pressure Pw2 in accordance with the first pressurizing mode, it is considered that the injection solution, which is confined in the penetrating passage having the reduced diameter, is pressurized again. However, the injection solution, which is allowed to inject in the second pressurizing mode, behaves to pressurize the skin structure by the aid of the injection solution existing at the unreduced diameter portion rather than to directly act on the bottom of the penetrating passage, on account of the difference in strength as described above. Therefore, the injection solution causes the permeation into the interior of the skin structure from the penetrating passage in the unreduced diameter state, rather than the further erosion in the depth direction. In other words, it is considered that the injection solution is diffused to the interior of the tissue of the skin structure via the portion of the penetrating passage in the unreduced diameter state which is considered to have the relatively low strength with respect to the pressure (in FIG. 5(b), the injection solution, which is diffused in accordance with the second pressurizing mode, is represented by S2). Further, the pressure increase rate, which is provided in the second pressurizing mode, is gentler than the pressure increase rate which is provided in the first pressurizing mode. Therefore, the injection solution can be diffused into the skin along the extending direction of the layered tissue of the skin structure without uselessly deepening the injection depth of the injection solution. FIG. 5(b) shows the diffusion state as described above merely conceptually. When the injection depth is set to any different depth as viewed in FIG. 5(a), the diffusion state differs as well. For example, it is also possible to effect the diffusion so that the injection solution is permeated into a portion disposed nearer to the dermis or into the dermis.

The period of time, in which the second pressurizing mode is continued, is determined depending on the amount of the injection solution (injection amount) allowed to inject by the syringe 1. After the passage of the second peak pressure P2max2, the pressure, which is applied to the injection solution, is gradually lowered. However, the pressure becomes zero at the point in time at which the injection solution allowed to inject from the nozzles 4 is exhausted, and the second pressurizing mode comes to the end. The purpose of the second pressurizing mode is to diffuse the injection solution to the desired depth of the skin structure. Therefore, it is preferable that the injection solution amount, which is allowed to inject from the syringe 1 in the second pressurizing mode, is larger than the injection solution amount which is allowed to inject in the first pressurizing mode. This situation can be sufficiently realized, because the first pressurizing mode is performed within the minute time Δt as described above.

In this way, in the case of the syringe 1 according to the present invention, the pressure transition advances such that the pressure undergoes the waiting pressure in the first pressurizing mode and the injection solution is diffused in accordance with the second pressurizing mode. Accordingly, the injection solution can be fed to the desired depth in the skin structure. In particular, the pressurization, which is performed in the second pressurizing mode, is principally directed to the diffusion of the injection solution, and the injection depth is prevented from being uselessly deepened. Therefore, it is possible to precisely diffuse the injection solution even at such a portion that the injection depth is relatively shallow.

An explanation will now be made about the pressure transitions L1, L2, L3 shown in FIG. 4 respectively. In these pressure transitions, the peak pressures, which are provided in the first pressurizing mode, are approximately P1max and coincident with each other by utilizing the same initiator 20. The waiting pressures are dispersed in a range of Pw1 to Pw3. However, as described above, as for the waiting pressure, when the pressure is lowered to some extent from the peak pressure in the first pressurizing mode, then the erosion caused by the discharging injection solution in the first pressurizing mode, which occurs in the injection depth direction at the inside of the skin structure, is mitigated, and the pressure may behave such a pressure that the diameter of the penetrating passage can be contracted or reduced at the part of the penetrating passage for the injection solution provided in the skin structure. In this way, even when the same initiator 20 is used, the gas generating agents 30, each of which is arranged in the combustion chamber 9, have the different amounts. Accordingly, the pressure transitions in the second pressurizing mode are changed as shown in FIG. 4. Specifically, in the case of the pressure transition L1, the amount of the gas generating agent 30 is maximized. In the case of the pressure transition L3, the amount of the gas generating agent 30 is minimized. In the case of the pressure transition L2, the amount of the gas generating agent 30 is the intermediate amount. Therefore, the peak pressures in the second pressurizing mode reside in a relationship of P2max1 in pressure transition L1>P2max2 in pressure transition L2>P2max3 in pressure transition L3. According to the three types of the pressure transitions as described above, it is possible to provide the different speeds to diffuse the injection solution and the different amounts of the injection solution to be diffused at approximately the same injection depth.

The peak pressure P2max3, which is provided in the pressure transition L3, has the value which is lower than that of the peak pressure P1max provided in the first pressurizing mode. In this procedure, the pressure difference between P1max and P2max3 is within a predetermined ratio with respect to P1max. This is because it is intended to clarify the pressure transition in which the injection solution is diffused in accordance with the second pressurizing mode after undergoing the waiting pressure in the first pressurizing mode, unlike any pressure transition based on the conventional technique, in order to feed the injection solution to the desired depth in the skin structure. The predetermined ratio is exemplified by 60% of P1max.

The peak pressures P2max1, P2max2, which are provided in the second pressurizing mode in the pressure transitions L1, L2, have the values which exceed the peak pressure P1max provided in the first pressurizing mode. The peak pressures P2max1, P2max2 as described above are appropriately set in order to realize the desired injection amounts.

The foregoing embodiment is explained assuming that the human skin structure is used. However, the syringe according to the present invention can be used as the syringe for animals (for example, farm animal, pet or the like) other than human. In this case, the type and the amount of the ignition charge 22 carried on the initiator 20 and the type and the amount of the gas generating agent 30 are appropriately adjusted while considering the characteristic of the skin structure of the injection target, for example, the Young's modulus or the like.

In the foregoing embodiment, the pressure is applied to the injection objective substance in the syringe 1. However, it is also allowable that the injection objective substance is, for example, a powder or a granular solid, provided that the injection objective substance can be allowed to inject from the syringe 1.

Examples

Experimental conditions and experimental results will now be described below in relation to injection experiments (Experiments 1 to 4) performed by using the syringe 1 according to the present invention. The following experimental conditions were set in order to diffuse the injection solution intensively or in a concentrated manner into the skin layer of a pig as an injection target.

Experimental Conditions (About Syringe 1)
87 mg of ZPP (zirconium and potassium perchlorate) mixture was used for the ignition charge 22 of the initiator 20, and single base propellant in an amount shown in Table 1 below was used for the gas generating agent 30. The diameter of the nozzle 4 is 0.1 mm, and the three nozzles 4 are arranged concentrically.

The component ratio of the single base propellant is as follows.
Nitrocellulose: 98.1% by weight;
Diphenylamine: 0.8% by weight;
Potassium sulfate: 1.1% by weight;
Graphite (loss ratio (outage)): minute amount.
(About Injection Target)
In this embodiment, a skin portion of abdomen of a pig was used as the injection target. Specifically, the pig was sacrificed, and then the skin portion was peeled off, followed by being stored for 6 days in a physiological saline solution at 4° C. to prepare a sample (cooled and stored), or followed by being frozen and stored at −70° C. and thawed thereafter to prepare a sample.
(About Injection Solution)
In order to easily grasp the diffusion situation of the injection solution after the injection, a colored aqueous solution (methylene blue) was used.

TABLE 1

| | Experiment 1 | Experiment 2 | Experiment 3 | Experiment 4 |
|---|---|---|---|---|
| Initiator | ZPP | ZPP | ZPP | ZPP |
| Amount of ignition charge | 87 mg | 87 mg | 87 mg | 87 mg |
| Amount of gas generating agent | Single base propellant 150 mg | Single base propellant 90 mg | Single base propellant 180 mg | Single base propellant 150 mg |
| Injection target | Frozen pig | Cooled pig | Cooled pig | Cooled pig |

Experimental Results

Figure 6A:
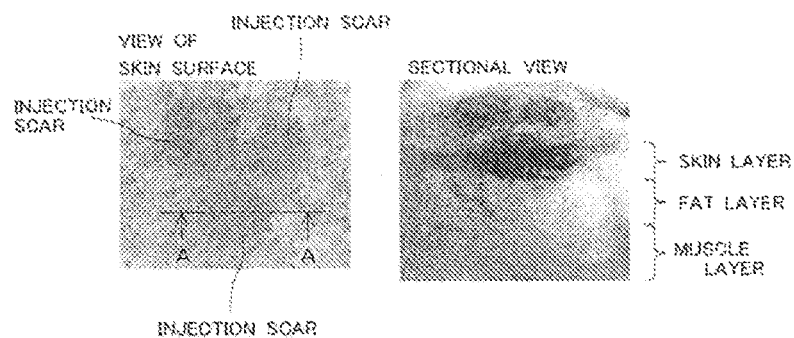
FIG. 6A shows a first view illustrating a result of an injection experiment by using the syringe according to the present invention.
Figure 6B:
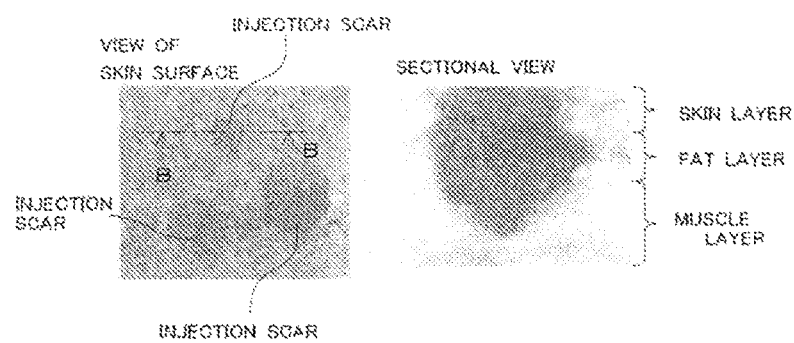
FIG. 6B shows a second view illustrating a result of an injection experiment by using the syringe according to the present invention.
Figure 6C:
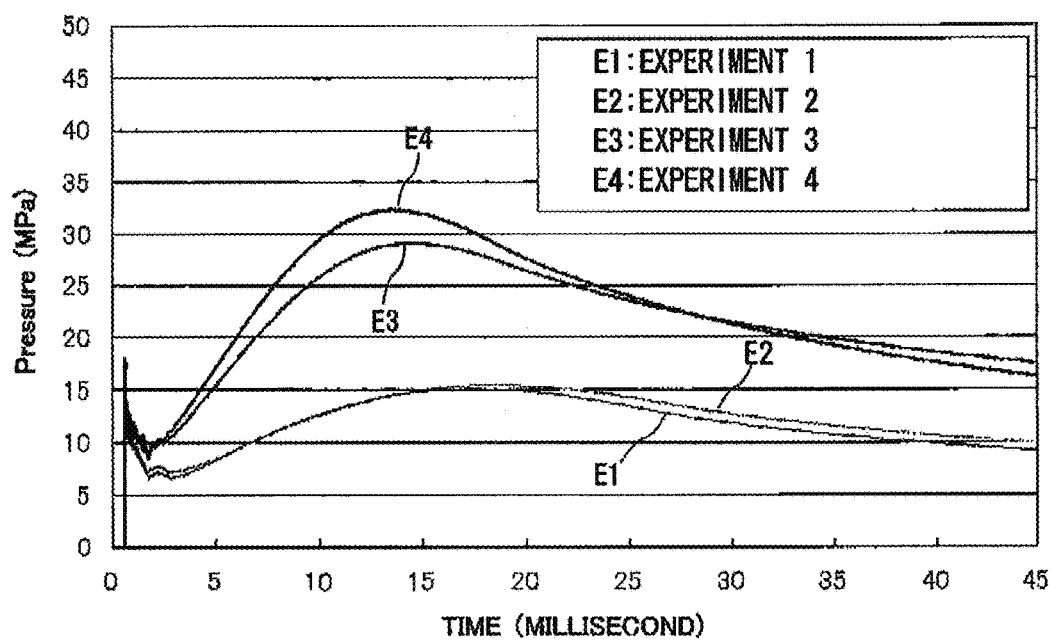
FIG. 6C shows a third view illustrating a result of an injection experiment by using the syringe according to the present invention.

Next, the experimental results as obtained in accordance with the foregoing experimental conditions are shown below. FIG. 6A shows a view illustrating a pig skin surface in relation to an injection result in Experiment 3 and a sectional view thereof (cross section taken along AA). On the other hand, FIG. 6B shows a view illustrating a pig skin surface in relation to an injection result in Experiment 4 and a sectional view thereof (cross section taken along BB). Further, FIG. 6C shows graphs illustrating the pressure transitions applied to the injection solution in Experiment 1 to Experiment 4 respectively. Table 2 shown below summarizes the predetermined pressure values in the pressure transitions and the times required to arrive at the pressures respectively. The pressure, which was applied to the injection solution, was measured by using an electrostrictive element (piezoelectric element) at a detection frequency of 100,000 times per second, i.e., every 0.01 millisecond. The maximum pressure, which was detected immediately after the operation of the initiator 20, was adopted for the first peak pressure shown in Table 2 below. An average value of the data was adopted for the waiting pressure, the data including the data as obtained within 0.05 ms before and after the minimum pressure (i.e., pieces of data obtained at respective five points provided therebefore and thereafter) recorded in such an interval that the pressure was lowered from the first peak pressure during the period in which the gas generating agent 30 was completely ignited after the operation of the initiator 20. The maximum pressure, which appeared after the arrival at the waiting pressure, was adopted for the second peak pressure. The respective times required to arrive shown in Table 2 mean the periods of time required until arrival at the respective pressures by using, as the start point, the point in time at which the ignition current was allowed to flow to the initiator 20.

TABLE 2

| | Exp. 1 | Exp. 2 | Exp. 3 | Exp. 4 |
|---|---|---|---|---|
| First peak pressure (MPa) | 16.8 | 17.5 | 18.0 | 17.4 |
| Time required to arrive at first peak pressure (ms) | 0.61 | 0.60 | 0.61 | 0.61 |
| Waiting pressure (MPa) | 6.73 | 7.39 | 8.95 | 8.84 |
| Time required to arrive at waiting pressure (ms) | 1.73 | 1.74 | 1.71 | 1.74 |
| Second peak pressure (MPa) | 15.1 | 15.4 | 32.3 | 29.2 |
| Time required to arrive at second peak pressure (ms) | 17.29 | 18.19 | 13.61 | 14.60 |
| Waiting pressure ratio (waiting pressure/ first peak pressure) | 0.40 | 0.42 | 0.50 | 0.51 |

The foregoing experimental results are analyzed as follows. That is, in Experiments 1, 2, and 3, the injection solution, which was allowed to inject from all of the three nozzles 4 provided for the syringe 1, was successfully diffused at the desired injection depth in the skin layer of the pig. For example, as shown in FIG. 6A corresponding to Experiment 3, as overlooked from the skin surface, it is appreciated that the injection scars are spread in approximately identical sizes at three positions. In the cross section, the injection solution is not uselessly spread to the fat layer and the muscle layer, and the injection solution is diffused in a state of staying in the skin layer. If the injection solution is vaccine, the vaccine can be fed and diffused intensively or in a concentrated manner to the area in which it can be expected to cause the effective antigen-antibody reaction. Also in Experiments 1 and 2 which are not shown, the effective diffusion of the injection solution was successfully confirmed in the same manner as in Experiment 3 shown in FIG. 6A.

On the other hand, in Experiment 4, as for the injection solution allowed to inject from one nozzle of the three nozzles 4, the injection solution is somewhat spread to the fat layer and the muscle layer unlike Experiments 1 to 3 (see a sectional view shown in FIG. 6B corresponding to Experiment 4). Further, as overlooked from the skin surface shown in FIG. 6B, it is acknowledged that the size of the injection scar corresponding to the sectional view is smaller than those of the injection scars formed at the other two positions. This is because the injection solution arrived at the deeper position of the injection target as shown in the sectional view in relation to the small injection scar, and the amount of the injection solution, which was successfully confirmed from the surface, was decreased. However, although not shown, the effective diffusion of the injection solution was successfully confirmed for the two nozzles other than the nozzle shown in FIG. 6B in the same manner as in Experiments 1 to 3.

Based on the foregoing fact, it is affirmed that when the waiting pressure ratio (defined as the value obtained by dividing the waiting pressure by the first peak pressure) has the value lower than the predetermined value, the injection solution, which is allowed to inject from at least any one of the nozzles 4, can be effectively diffused into the skin layer of the pig, wherein it is possible to find out the significance of practical use. More preferably, when the waiting pressure ratio is not more than 0.50, it is considered that the effective diffusion is realized for the injection solution allowed to inject from all of the three nozzles 4 as shown in Experiments 1 to 3. In the case of any conventional needle-free syringe, the injection solution has been fed to the deep inside of the injection target to such an extent that the injection scar cannot be confirmed even by being overlooked from the skin surface unlike the present invention. Taking this fact into consideration, it is affirmed that the syringe 1 according to the present invention provides the useful effect which can be never realized by the conventional needle-free syringe.

Other Examples

According to the syringe 1 of the present invention, for example, cultured cells or stem cells can be seeded or inoculated with respect to cells or scaffold tissue (scaffold) as the injection target in the field of the regenerative medicine, other than the case in which the injection solution is injected into the skin structure as described above. For example, as described in JP2008-206477A, it is possible to inject, by the syringe 1, cells which may be appropriately determined by those skilled in the art depending on the portion subjected to the transplantation and the purpose of the cell regeneration, for example, endothelial cell, endothelial precursor cell, myeloid cell, preosteoblast, chondrocyte, fibroblast, skin cell, muscle cell, liver cell, kidney cell, intestinal tract cell, and stem cell, as well as every cell considered in the field of the regenerative medicine. More specifically, a solution (cell suspension) containing the cells to be seeded or inoculated as described above is accommodated in the through-hole 14 by using the sealing members 7, 8, for which the pressurization is performed in accordance with the pressure transition based on the first pressurizing mode and the second pressurizing mode as described above. Accordingly, the predetermined cells are injected and transplanted to the portion subjected to the transplantation.

Further, the syringe 1 according to the present invention can be also used to deliver DNA or the like, for example, to cells or scaffold tissue (scaffold) as described in JP2007-525192W. In this case, it is possible to suppress the influence exerted, for example, on cells themselves or scaffold tissue (scaffold) itself when the syringe 1 according to the present invention is used, as compared with when the delivery is performed by using any needle. Therefore, it is affirmed that the use of the syringe 1 according to the present invention is more preferred.

Further, the syringe 1 according to the present invention is also preferably used, for example, when various genes, cancer suppressing cells, or lipid envelops are directly delivered to the objective tissue and when the antigen gene is administered in order to enhance the immunity against the pathogen. Other than the above, the syringe 1 can be also used, for example, for the field of the medical treatment for various diseases (field as described, for example, in JP2008-508881 and JP2010-503616) and the field of the immunological medical treatment (immunotherapy) (field as described, for example, in JP2005-523679). The field, in which the syringe 1 is usable, is not intentionally limited.

PARTS LIST

1: syringe, 2: main syringe body, 4: nozzle, 5: holder, 6: piston, 7, 8: sealing member, 9: combustion chamber, 10: recess, 11: flow passage, 20: initiator, 22: ignition charge, 30: gas generating agent.

What is claimed is:

1. A syringe for injecting an injection objective substance into an injection target area of a living body without using any injection needle, the syringe comprising:
   an enclosing unit which encloses the injection objective substance;
   an ignition device which includes an ignition charge and flows an ignition current so that the ignition charge is combusted;
   a combustion chamber into which the combustion product produced by combustion of the ignition charge is allowed to flow and which accommodates a gas generating agent that is to be combusted by the combustion product to produce a predetermined gas;
   a pressurizing unit which pressurizes the injection objective substance enclosed in the enclosing unit; and
   a flow passage unit which defines a flow passage so that the injection objective substance, which is pressurized by the pressurizing unit, is allowed to inject to the injection target area,
   wherein the pressurizing unit has:
   a first pressurizing mode in which a pressure applied to the injection objective substance in the pressurizing unit is raised to a first peak pressure in order to allow the injection objective substance to penetrate through a surface of the injection target area, and then the pressure applied to the injection objective substance is lowered to a waiting pressure; and
   a second pressurizing mode in which the injection objective substance having the waiting pressure is pressurized so that the pressure applied to the injection objective substance is raised to a second peak pressure to inject a predetermined injection amount of the injection objective substance,
   wherein a time, until the pressure applied to the injection objective substance is raised to the first peak pressure and then is lowered to the waiting pressure after the ignition current is allowed to flow to the ignition device, is within 2 msec.

2. The syringe according to claim 1, wherein the pressure applied to the injection objective substance reaches the waiting pressure within 1.7 msec after the ignition current is allowed to flow to the ignition device.

3. The syringe according to claim 1, wherein the waiting pressure is not more than 50% of the first peak pressure.

4. The syringe according to claim 1, wherein:
   the second peak pressure is not more than the first peak pressure; and
   a pressure difference between the first peak pressure and the second peak pressure is within 60% with respect to the first peak pressure.

5. The syringe according to claim 1, wherein the second peak pressure is a pressure which exceeds the first peak pressure.

6. The syringe according to claim 1, wherein a rate of pressure increase, which is provided from the waiting pressure to arrival at the second peak pressure in the second pressurizing mode, is lower than a rate of pressure increase which is provided from start of pressurization to arrival at the first peak pressure in the first pressurizing mode.

7. The syringe according to claim 1, wherein an amount of the injection objective substance in the second pressurizing mode is larger than an amount of the injection objective substance in the first pressurizing mode.

8. The syringe according to claim 1, wherein:
   a combustion completion time of the ignition charge comes earlier than a combustion completion time of the gas generating agent; and
   a velocity of production of the gas from the gas generating agent is increased at a stage at which the combustion of the ignition charge is completed and the pressure applied to the injection objective substance is decreased from the first peak pressure to the waiting pressure.

9. The syringe according to claim 1, wherein the ignition charge is any one of explosive charges of an explosive charge containing zirconium and potassium perchlorate, an explosive charge containing titanium hydride and potassium perchlorate, an explosive charge containing titanium and potassium perchlorate, an explosive charge containing aluminum and potassium perchlorate, an explosive charge containing aluminum and bismuth oxide, an explosive charge containing aluminum and molybdenum oxide, an explosive charge containing aluminum and copper oxide, and an explosive charge containing aluminum and iron oxide, or an explosive charge composed of a combination of a plurality of the foregoing explosive charges.

* * * * *